(12) United States Patent
Zamora et al.

(10) Patent No.: US 9,078,773 B2
(45) Date of Patent: Jul. 14, 2015

(54) PROSTHETIC FOOT

(75) Inventors: David A. Zamora, Mesa, AZ (US); Keith B. Smith, Gilbert, AZ (US); Adam A. Ochoa, Scottsdale, AZ (US)

(73) Assignee: Ability Dynamics LLC, Tempe, AZ (US)

( * ) Notice: Subject to any disclaimer, the term of this patent is extended or adjusted under 35 U.S.C. 154(b) by 29 days.

(21) Appl. No.: 13/642,501

(22) PCT Filed: Apr. 20, 2011

(86) PCT No.: PCT/US2011/033319
§ 371 (c)(1),
(2), (4) Date: Nov. 27, 2012

(87) PCT Pub. No.: WO2011/133717
PCT Pub. Date: Oct. 27, 2011

(65) Prior Publication Data
US 2013/0066439 A1     Mar. 14, 2013

Related U.S. Application Data

(63) Continuation-in-part of application No. 12/799,215, filed on Apr. 20, 2010, now abandoned, which is a continuation-in-part of application No. 11/901,845, filed on Sep. 19, 2007, now Pat. No. 8,048,173.

(51) Int. Cl.
*A61F 2/68* (2006.01)
*A61F 2/66* (2006.01)
(Continued)

(52) U.S. Cl.
CPC ... *A61F 2/66* (2013.01); *A61F 2/60* (2013.01); *A61F 2002/30164* (2013.01); *A61F 2002/30359* (2013.01); *A61F 2002/30387* (2013.01); *A61F 2002/30434* (2013.01);
(Continued)

(58) Field of Classification Search
CPC ..................................... A61F 2/60; A61F 2/66
See application file for complete search history.

(56) References Cited

U.S. PATENT DOCUMENTS

| 4,822,363 A | 4/1989 | Phillips |
| 5,116,384 A | 5/1992 | Wilson et al. |

(Continued)

FOREIGN PATENT DOCUMENTS

| WO | 93/24080 A1 | 12/1993 |
| WO | 2006/099580 A2 | 9/2006 |

OTHER PUBLICATIONS

Roland D. Christensen, U.S. Appl. No. 09/607,494 for "Prosthetic foot," filed Jun. 30, 2000, abandoned Oct. 29, 2002.

*Primary Examiner* — Jacqueline Woznicki
(74) *Attorney, Agent, or Firm* — The Noblitt Group, PLLC

(57) ABSTRACT

A prosthetic foot comprises a ground engaging bottom resilient member, a resilient heel member, and a resilient toe member that collectively circumscribe an open volumetric space. The members resilient compress to absorb compressive force throughout the entire stride of an individual utilizing the foot. The prosthetic foot stores energy during a heel strike phase of a gait cycle, and releases energy during a toe-off phase of the gait cycle in order to assist forward movement of a user. During the gait cycle, a loading response during the heel strike phase compresses the heel member and the toe member, and causes a deflection of the rear portion of the bottom member. Furthermore, an upward deflection of at least one of the bottom member and the toe member stores energy during the transition from the heel strike phase to the toe-off phase of the gait cycle.

16 Claims, 16 Drawing Sheets

(51) Int. Cl.
   *A61F 2/50*   (2006.01)
   *A61F 2/60*   (2006.01)
   *A61F 2/30*   (2006.01)

(52) U.S. Cl.
   CPC   *A61F 2002/5003* (2013.01); *A61F 2002/5007* (2013.01); *A61F 2002/6614* (2013.01); *A61F 2002/6621* (2013.01); *A61F 2002/6642* (2013.01); *A61F 2002/6657* (2013.01); *A61F 2002/6671* (2013.01); *A61F 2002/6692* (2013.01); *A61F 2220/0025* (2013.01); *A61F 2220/0033* (2013.01); *A61F 2220/0041* (2013.01); *A61F 2230/0028* (2013.01)

(56)   References Cited

U.S. PATENT DOCUMENTS

| | | | |
|---|---|---|---|
| 5,944,760 A | 8/1999 | Christensen | |
| 6,120,547 A | 9/2000 | Christensen | |
| 6,197,068 B1 | 3/2001 | Christensen | |
| 6,241,776 B1 | 6/2001 | Christensen | |
| 6,663,673 B2 | 12/2003 | Christensen | |
| 6,702,858 B2 | 3/2004 | Christensen | |
| 6,767,370 B1 * | 7/2004 | Mosler et al. | 623/55 |
| 6,805,717 B2 | 10/2004 | Christensen | |
| 6,875,241 B2 | 4/2005 | Christensen | |
| 6,875,242 B2 | 4/2005 | Christensen | |
| 6,911,052 B2 | 6/2005 | Christensen | |
| 6,929,665 B2 | 8/2005 | Christensen | |
| 6,942,704 B2 | 9/2005 | Sulprizio | |
| 6,966,933 B2 | 11/2005 | Christensen | |
| 7,063,727 B2 | 6/2006 | Phillips et al. | |
| 7,172,630 B2 | 2/2007 | Christensen | |
| 7,178,218 B1 * | 2/2007 | Houser et al. | 29/558 |
| 7,341,603 B2 | 3/2008 | Christensen | |
| 7,419,509 B2 | 9/2008 | Christensen | |
| 7,462,201 B2 | 12/2008 | Christensen | |
| 7,520,904 B2 | 4/2009 | Christensen | |
| 7,572,299 B2 | 8/2009 | Christensen | |
| 7,618,464 B2 | 11/2009 | Christensen | |
| 7,655,050 B2 | 2/2010 | Palmer | |
| 7,686,848 B2 | 3/2010 | Christensen | |
| 7,727,285 B2 | 6/2010 | Christensen | |
| 7,740,602 B2 | 6/2010 | Christensen | |
| 7,794,506 B2 | 9/2010 | Christensen | |
| 7,824,446 B2 | 11/2010 | Christensen | |
| 8,034,121 B2 | 10/2011 | Christensen | |
| 8,070,828 B2 | 12/2011 | Shannon | |
| 2003/0109638 A1 | 6/2003 | Briggs et al. | |
| 2005/0038525 A1 | 2/2005 | Doddroe | |
| 2005/0203640 A1 | 9/2005 | Christensen | |
| 2005/0216098 A1 | 9/2005 | Christensen | |
| 2006/0069450 A1 * | 3/2006 | McCarvill et al. | 623/55 |
| 2006/0224246 A1 | 10/2006 | Clausen | |
| 2006/0241783 A1 | 10/2006 | Christensen | |
| 2008/0033578 A1 | 2/2008 | Christensen | |
| 2008/0228288 A1 | 9/2008 | Nelson et al. | |
| 2009/0076626 A1 * | 3/2009 | Ochoa | 623/55 |
| 2010/0042228 A1 | 2/2010 | Doddroe et al. | |
| 2011/0009982 A1 | 1/2011 | King et al. | |
| 2011/0197682 A1 | 8/2011 | Palmer | |
| 2011/0199101 A1 | 8/2011 | Steele | |
| 2011/0202144 A1 | 8/2011 | Palmer | |
| 2011/0208322 A1 | 8/2011 | Rifkin et al. | |
| 2011/0320012 A1 | 12/2011 | Christensen et al. | |
| 2012/0046760 A1 | 2/2012 | Nissels et al. | |
| 2012/0179274 A1 | 7/2012 | Christensen | |
| 2012/0209406 A1 | 8/2012 | Chen et al. | |
| 2012/0271434 A1 | 10/2012 | Friesen et al. | |
| 2013/0173023 A1 | 7/2013 | Lecomte et al. | |
| 2014/0156027 A1 * | 6/2014 | Smith et al. | 623/54 |

* cited by examiner

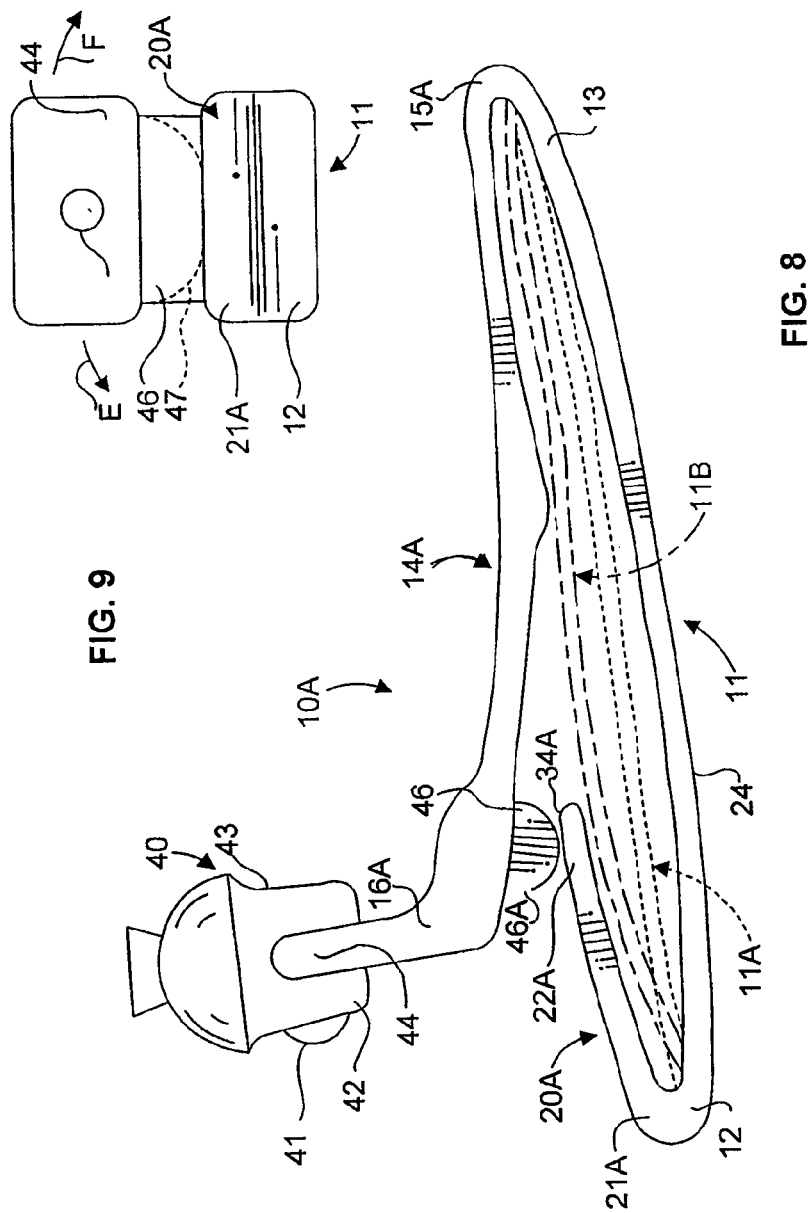

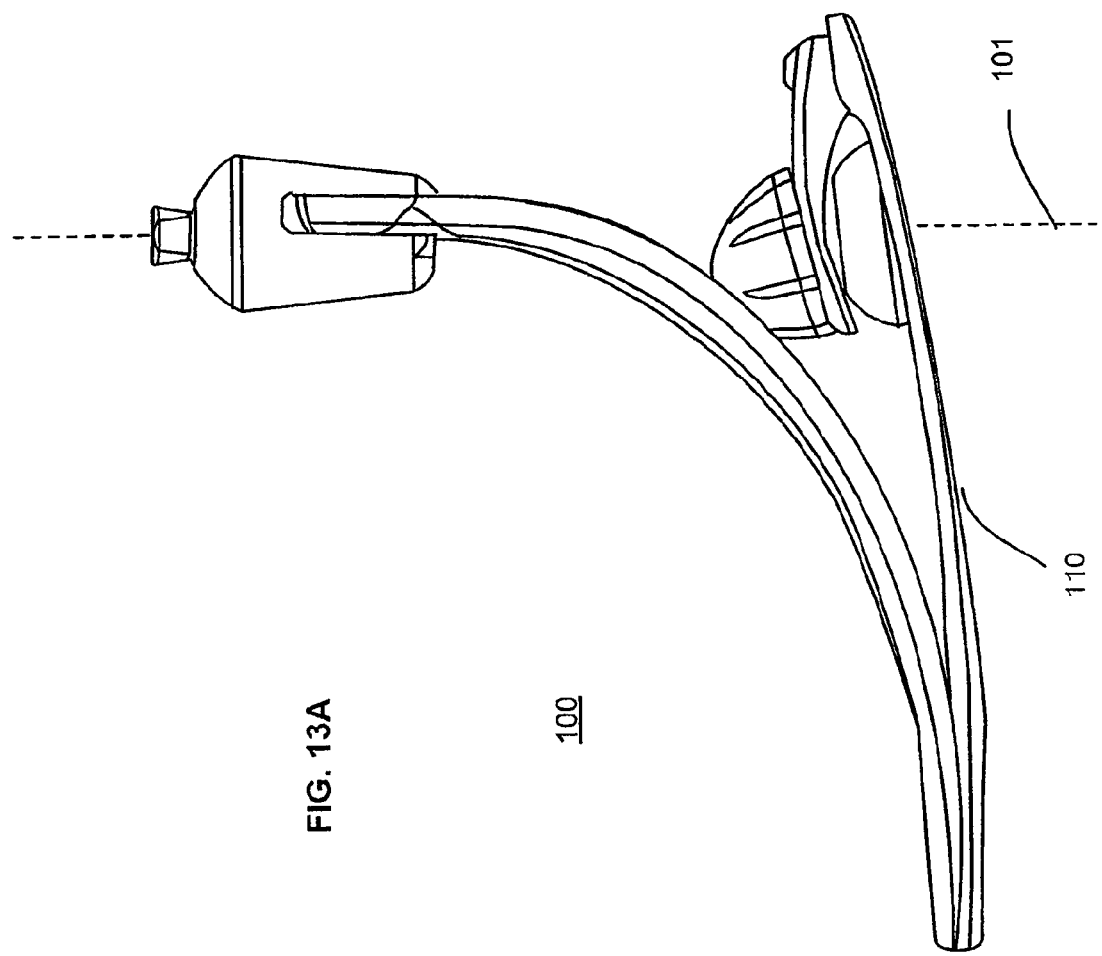

PROSTHETIC FOOT

CROSS-REFERENCE TO RELATED APPLICATIONS

This application is the U.S. National Phase of International Application No. PCT/US2011/033319, filed on Apr. 20, 2011, which is a continuation-in-part of U.S. application Ser. No. 12/799,215, filed Apr. 20, 2010; and the '215 application is a continuation-in-part of U.S. patent application Ser. No. 11/901,845, filed Sep. 19, 2007, all of which are hereby incorporated by reference.

FIELD OF THE INVENTION

This invention pertains to prosthetic devices. More particularly, the invention pertains to a prosthetic foot that, when utilized by an amputee, better replicates the action of a real foot and reduces the risk of injury to the amputee.

BACKGROUND OF THE INVENTION

Prosthetic feet are well known in the art. In use, such prosthetic feet typically do not replicate the action of a real foot and can generate "kickback" or "kickforward" reactions that increase the risk of injury to an amputee utilizing the foot. Kickback is motion created by the prosthetic foot in a backward direction during the walking cycle. Kickforward is motion created by the prosthetic foot in a forward direction during the walking cycle. Either motion may create instability for user if expanding or restricting the intended motion.

For an amputee, loosing bipedality may produce an involuntary anterior lean or shift, forcing a constant imbalance or rebalance of posture. The amputee no longer posses voluntary muscle control on his involved side due to the severance of the primary flexor and extensor muscles. The primary anterior muscle responsible for dorsiflexion (sagittal plane motion) is the anterior tibialis. Dorsiflexion is the voluntary ankle motion that elevates the foot upwards, or towards the midline of the body. The primary posterior muscle responsible for plantarflexion is is the gastro-soleus complex. It is a combination of two muscles working in conjunction: the gastrocnemius and the soleus. Plantarflexion is the voluntary ankle motion that depresses the foot downwards, or away from the midline of the body. Therefore, it is desirable to have a prosthetic foot configured to promote increased muscle activity and promote increased stability for amputees, and it is desirable to provide an improved prosthetic foot which would better replicate the action of a true foot. Furthermore, it is desirable to provide an improved prosthetic foot which minimizes or eliminates "kickback" forces when the foot is utilized to walk over a door jamb or other raised profile object on a floor or on the ground.

SUMMARY OF THE INVENTION

An exemplary prosthetic foot is capable of mimicking the weight-bearing action and momentum supplied by a foot. The exemplary prosthetic foot approximates the feel and range of motion of a user's normal stride. In one embodiment, a prosthetic foot comprises a bottom member, a heel member attached to a rear portion of the bottom member, and a toe member attached to a front portion of the bottom member. The prosthetic foot is configured to store energy during a heel strike phase of a gait cycle, and release energy during a toe-off phase of the gait cycle in order to assist forward movement of a user. During the gait cycle, a loading response during the heel strike phase compresses the heel member and the toe member, and causes a deflection of the rear portion of the bottom member. Furthermore, an upward deflection of at least one of the bottom member and the toe member stores energy during the transition from the heel strike phase to the toe-off phase of the gait cycle.

In another embodiment, a prosthetic foot comprises a resilient bottom member having a first bottom end and a second bottom end, a resilient toe member having a first toe end and a second toe end, and a resilient heel member having a first heel end and a second heel end. The first toe end is connected to the second bottom end of the resilient bottom member, and the resilient toe member is positioned over the resilient bottom member and directed towards the back of the prosthetic foot. The first heel end of the heel member is connected to the first bottom end of the resilient bottom member, and the resilient heel member is positioned over the resilient bottom member and directed towards the front of the prosthetic foot. An open volumetric space is formed by the resilient bottom member, the resilient heel member, and the resilient toe member. The resilient heel member and the resilient toe member may overlap to form the open volumetric space.

BRIEF DESCRIPTION OF THE DRAWINGS

These and other features, aspects and advantages of the present invention will become better understood with reference to the following description, appending claims, and accompanying drawings where:

FIG. 8 is a side view illustrating alternate embodiments of the prosthetic foot of FIG. 2;

FIG. 9 is a back view further illustrating the prosthetic foot of FIG. 8;

FIG. 13A is a side view of an exemplary prosthetic foot with a convex bottom surface;

DETAILED DESCRIPTION

Figure 1:
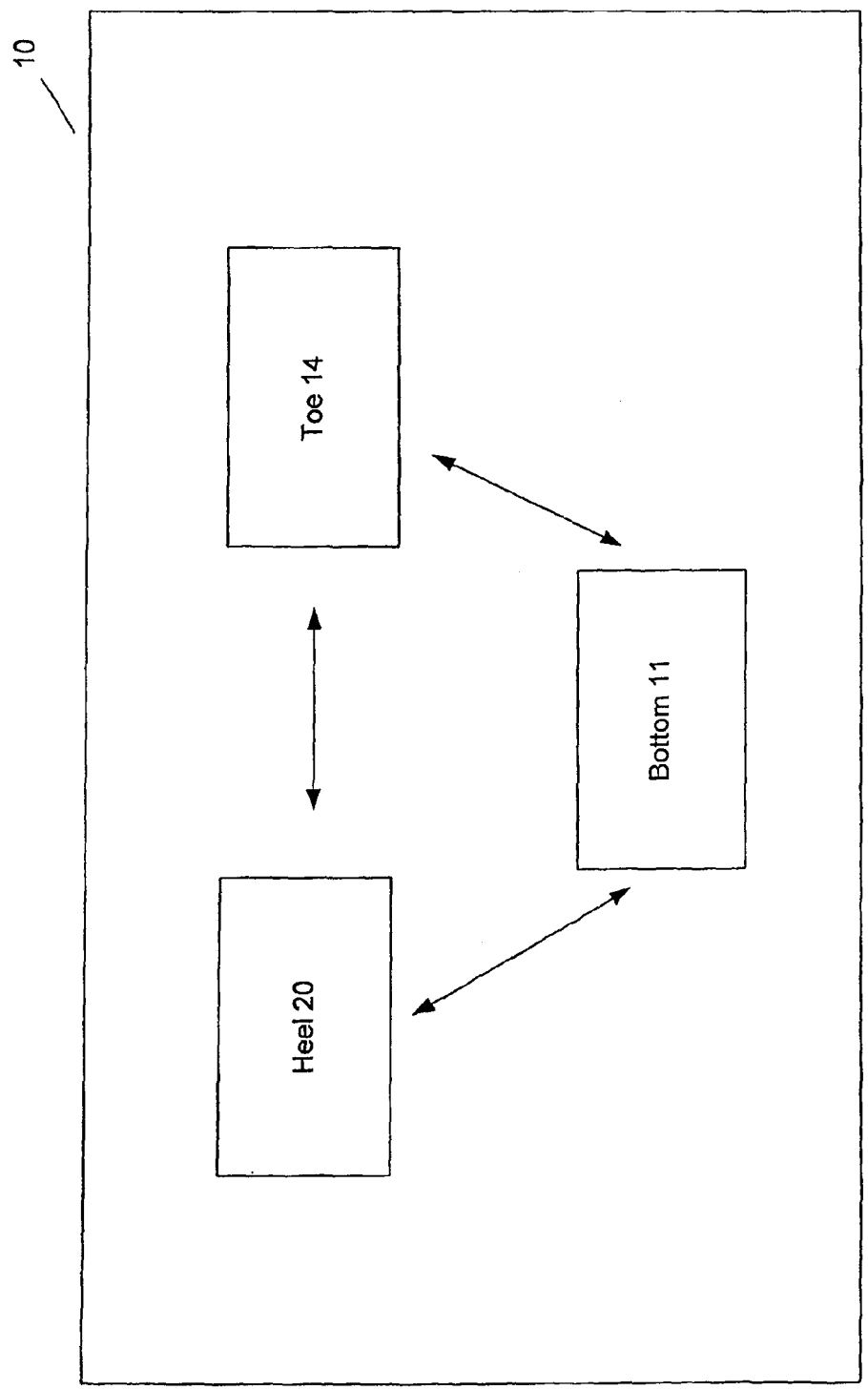
FIG. 1 is a block diagram illustrating the component interaction of an exemplary prosthetic foot.

While exemplary embodiments are described herein in sufficient detail to enable those skilled in the art to practice the invention, it should be understood that other embodiments may be realized and that logical structural and mechanical changes may be made without departing from the spirit and scope of the invention. Thus, the following descriptions are not intended as a limitation on the use or applicability of the invention, but instead, are provided merely to enable a full and complete description of exemplary embodiments.

Briefly, in accordance with an exemplary embodiment, a prosthetic foot has improvements over a prior art prosthetic foot in that a more natural motion and response of the foot occurs during movement. In particular, the movement of the exemplary prosthetic foot replicates the natural flex of a foot and supplies continuous energy to a person when striding from heel to toe. With respect to general structure in an exemplary embodiment, a prosthetic foot comprises a ground engaging bottom resilient member having a front end and a back end and an intermediate section spanning between and connecting the front end and the back end; a heel resilient member having a rear end connected to the back end of the bottom resilient member, extending upwardly from the back end, and, having a forward end spaced apart from the rear end and the bottom resilient member; and, a toe resilient member having a proximate end connected to the front end of the bottom member, extending upwardly from the front end and over the forward end of the heel resilient member, and having a distal end spaced apart from the proximate end, from the front end, and above the heel resilient member. The bottom member, heel member, and toe member are shaped and dimensioned and have a resistance response to a compressive applied force such that when the compressive applied force compresses said prosthetic foot against the ground the intermediate section of the bottom member upwardly deflects from the ground, and the toe member downwardly deflects toward the ground and contacts the heel resilient member and deflects the heel member toward the ground and toward the bottom member.

In another embodiment, a prosthetic foot comprises a ground engaging bottom resilient member having a front end and a back end and an intermediate section spanning between and connecting the front end and the back end; a toe resilient member having a rear end connected to the front end of the bottom resilient member, extending upwardly from the front end, and, having a forward end spaced apart from the rear end and the bottom resilient member; and, a heel resilient member having a proximate end connected to the back end of the bottom member, extending upwardly from the back end and over the forward end of the toe resilient member, and having a distal end spaced apart from the proximate end, from the back end, and above the toe resilient member. The bottom member, heel member, and toe member are shaped and dimensioned and have a resistance response to a compressive applied force such that when the compressive applied force compresses the prosthetic foot against the ground the intermediate section of the bottom member upwardly deflects from the ground, and, the heel member downwardly deflects toward the ground and contacts the toe resilient member and deflects the toe member toward the ground and toward the bottom member.

In accordance with an exemplary embodiment, and with reference to FIG. 1, a prosthetic foot 10 comprises a bottom member 11, a heel member 20, and a toe member 14. The three members 10, 14, 20 are structurally connected to form prosthetic foot 10 and configured to provide a natural stride for a user. In the exemplary embodiment, prosthetic foot 10 stores energy during the gait cycle and transfers the energy in order to "put a spring in your step." The gait cycle, and specifically the stance phase, includes a heel strike phase, the mid-stance phase, and the toe-off phase. The heel strike phase begins when the heel of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe.

Moreover, the three members 11, 14, 20 transfer energy between themselves in a natural, true foot manner, as indicated by the arrows in FIG. 1. The loading response during the heel strike phase compresses heel member 20 and toe member 14, which in turn passes energy into, and causes a deflection of, a rear portion of bottom member 11. Energy is transferred towards the front of prosthetic foot 10 during the mid-stance phase. Furthermore, an upward deflection of at least one of bottom member 11 and toe member 14 stores energy during the transition from the mid-stance phase to the toe-off phase of the gait cycle. In an exemplary embodiment, about 90% or more of the heel strike loading energy is stored and transferred to toe member 12 for assisting the toe-off phase. In another exemplary embodiment, about 95% or more of the heel strike loading energy is stored and transferred to toe member 12 for assisting the toe-off phase. In yet another exemplary embodiment, about 98% or more of the heel strike loading energy is stored and transferred to toe member 12 for assisting the toe-off phase. Prosthetic foot 10 may be designed to release the stored energy during the toe-off phase and assist in propelling the user in a forward direction.

Figure 2:
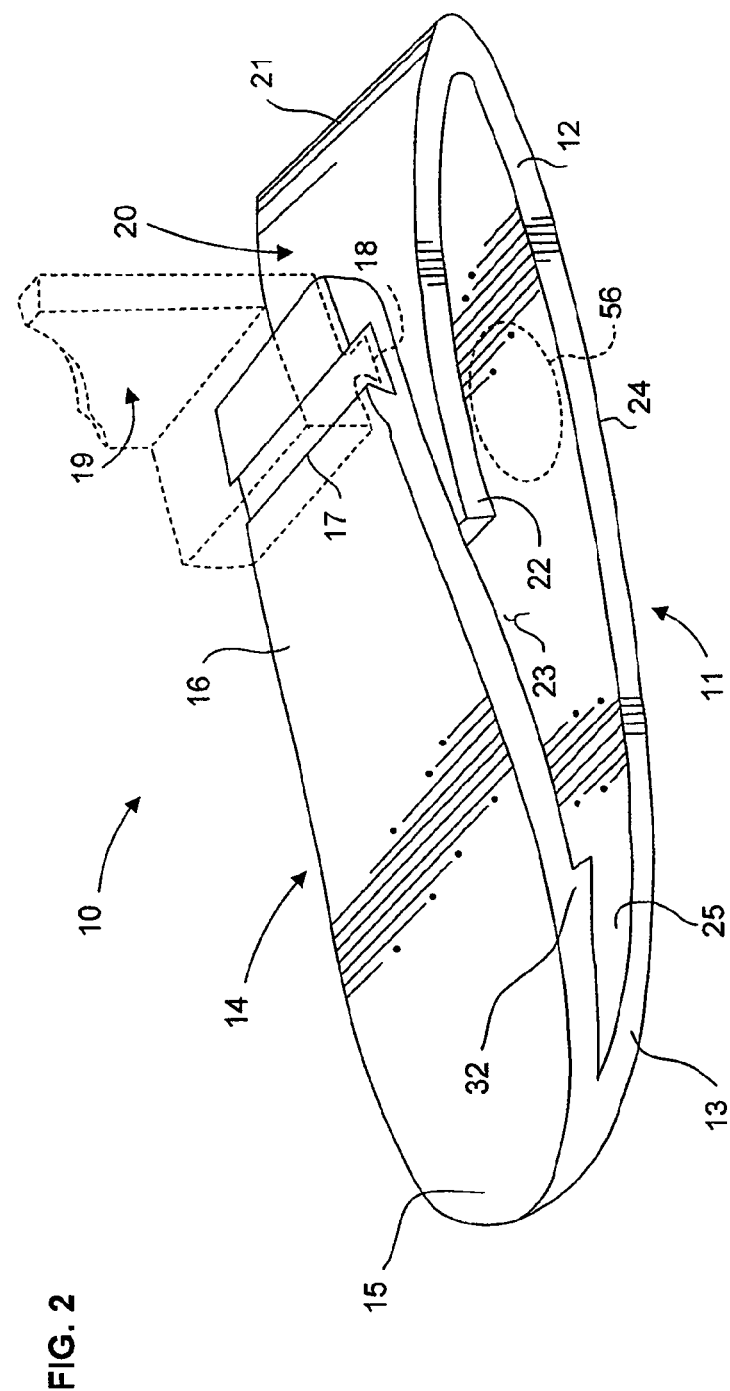
FIG. 2 is a perspective view illustrating a prosthetic foot constructed in accordance with an exemplary embodiment.

Turning now to the additional drawings, which depict the exemplary embodiments for the purpose of illustrating the practice thereof and not by way of limitation of the scope of the invention, and in which like reference characters refer to corresponding elements throughout the several views, FIGS. 2 to 7 illustrate one exemplary embodiment of a prosthetic foot In accordance with an exemplary embodiment, and with reference to FIG. 2, a prosthetic foot 10 comprises a first resilient flexion bottom member 11, a second resilient flexion heel member 20, and a third resilient flexion toe member 14. The three resilient members 11, 14, 20 are structurally connected to form prosthetic foot 10 and configured to provide a natural stride for a user. In one particular embodiment and with continued reference to FIG. 2, first resilient flexion bottom member 11 includes a first bottom end 12 and a second bottom end 13, second resilient flexion heel member 20 includes a first heel end 21 and a second heel end 22, and third resilient flexion toe member 14 includes a first toe end 15 and a second toe end 16. First heel end 21 of second resilient flexion heel member 20 may be connected to first bottom end 12 of first resilient flexion bottom member 11. Furthermore, first toe end 15 of third resilient flexion toe member 14 may be connected to second bottom end 13 of first resilient flexion bottom member 11. In an exemplary embodiment, second heel end 22 can, if desired, be fixedly secured to resilient flexion toe member 14. In an exemplary embodiment, resilient flexion members 11, 14, 20 may be fabricated together as a unitary member. In another embodiment, the end pairs 21-12 and 13-15 of resilient flexion members 11, 14, 20 may be connected with adhesive, bolts, or any other desired fastener or fastening means. For example, an elastomeric washer layer may be placed between first toe end 15 and second bottom end 13, and adhesive layers on either side of the washer may be used to hold the components together. The elastomeric layer may be neoprene, vulcanized rubber, polyurethane, or the like. Additionally, a layer placed between first toe end 15 and second bottom end 13 to facilitate attachment of the members may be various shapes and various materials as would be known to one skilled in the art. When prosthetic foot 10 is compressed against the ground, resilient flexion members 11, 14, 20 flex and have a resistance response in which flexed members 11, 14, 20 generate forces resisting such compression.

Furthermore, in an exemplary embodiment, prosthetic foot 10 may be configured to attach to a prosthetic leg. For example, second toe end 16 may be shaped and dimensioned and adapted to be connected to another portion of a leg prosthesis. By way of example, and not limitation, in FIG. 2 a trapezoidal slot 17 is formed in second toe end 16 to slidably receive a trapezoidal finger 18 of an L-shaped member 19 that forms a part of a leg prosthesis. In another example, and as illustrated in FIG. 8, an alternate way comprises shaping an end 16A of a flexible member 14 to facilitate attachment of a prosthetic foot 10A to the lower end of a prosthetic leg, or to a prosthetic device attached to the remaining portion of an individual's leg.

Figure 3:
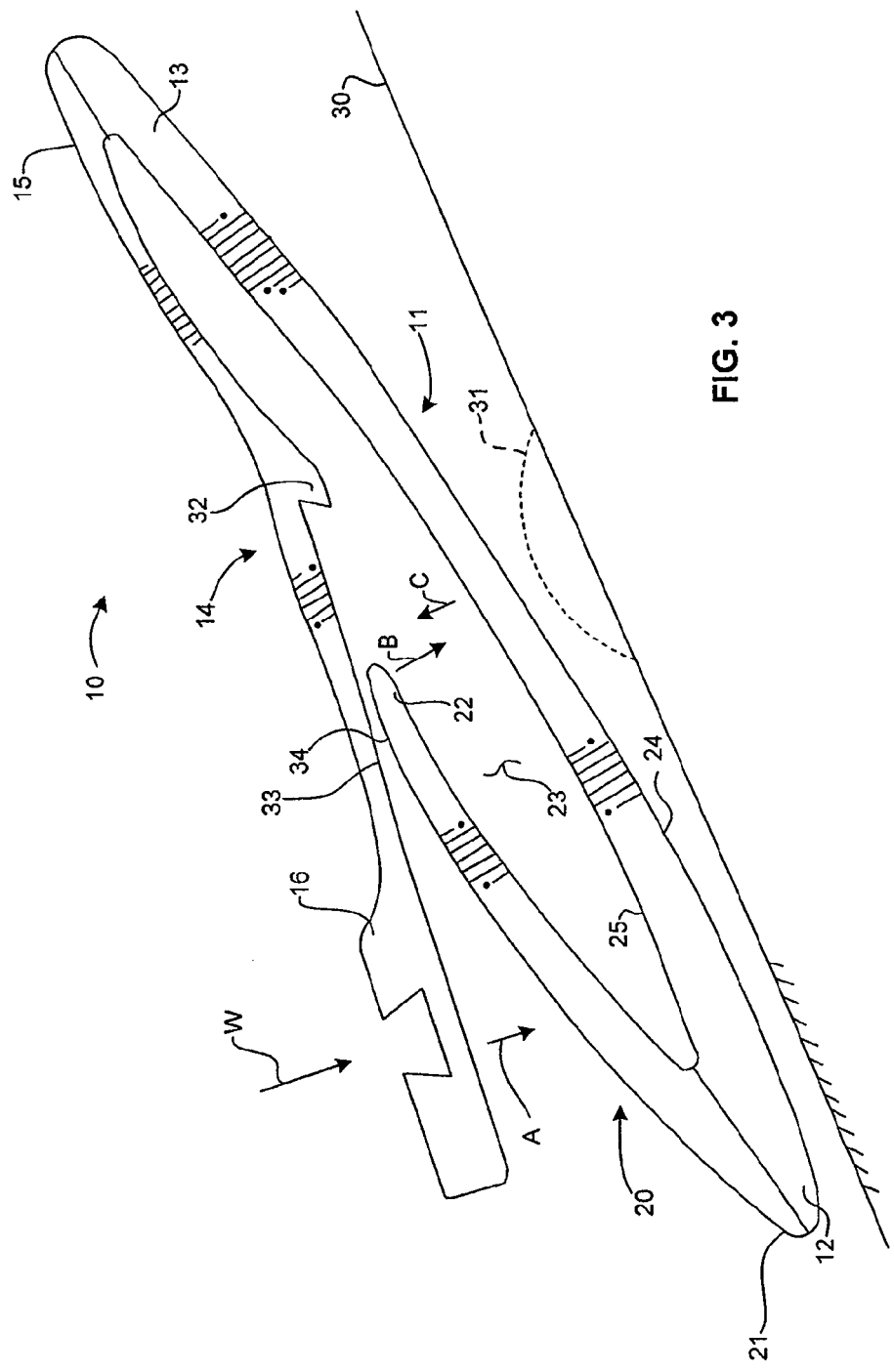
FIG. 3 is a side view further illustrating the prosthetic foot of FIG. 2 prior to impact.

In an exemplary embodiment and with reference to FIG. 3, resilient flexion bottom member 11 includes a bottom surface 24 and an upper surface 25. Resilient flexion heel member 20 includes upper contact surface 34. Resilient flexion toe member 14 includes lower contact surface 33, and includes a ridge 32. When prosthetic foot 10 is compressed and resilient flexion toe member 14 is compressed and displaced downwardly toward resilient flexion bottom member 11, ridge 32 can contact upper surface 25 and permit the portion of resilient flexion toe member 14 behind ridge 32 to continue to be downwardly depressed against resilient flexion heel member 20 and towards resilient flexion bottom member 11.

The compression of the prosthetic foot during motion results in the prosthetic foot changing shape. With respect to changing shape, resilient flexion members 11, 14, 20 extend around and partially enclose an open volumetric space 23. When prosthetic foot 10 is compressed to force resilient flexion members 14 and 20 toward resilient flexion bottom member 11, the volume, or size, of space 23 decreases. As is understood, once the compression forces are withdrawn from prosthetic foot 10, resilient flexion members 14 and 20 expand away from resilient flexion bottom member 11, and the volume, or size, of space 23 increases.

As would be appreciated by those of skill in the art, prosthetic foot 10 can, for aesthetic reasons, be inserted in a hollow, pliable, resilient replica of a foot that is made from rubber, another polymer, or another material. The use of such a housing or some other desired covering for prosthetic foot 10 ordinarily will not alter the functioning of prosthetic foot 10 as described herein.

For increased understanding of the exemplary embodiments, in FIGS. 3 to 6, it is assumed that prosthetic foot 10 is mounted on the lower end of a prosthetic device, that the prosthetic device and prosthetic foot 10 are mounted on an amputee or other individual and form at least a portion of an individual's leg, and that the individual is walking and is therefore utilizing the prosthetic device and prosthetic foot 10 mounted on the lower end thereof. A ground, floor, or other surface 30 illustrated in FIGS. 3 to 6 is variously shown as sloped upwardly, sloped downwardly, or level; this to indicate that the foot 10 generally functions in a similar manner on sloped or flat surfaces.

FIG. 3 illustrates prosthetic foot 10 just prior to heel strike. At heel strike on ground 30, prosthetic foot 10 is generally in front of the individual's upper body, as is normally the case when a person is walking. As previously discussed, energy storage occurs in prosthetic foot 10 as part of the loading response.

Figure 4:
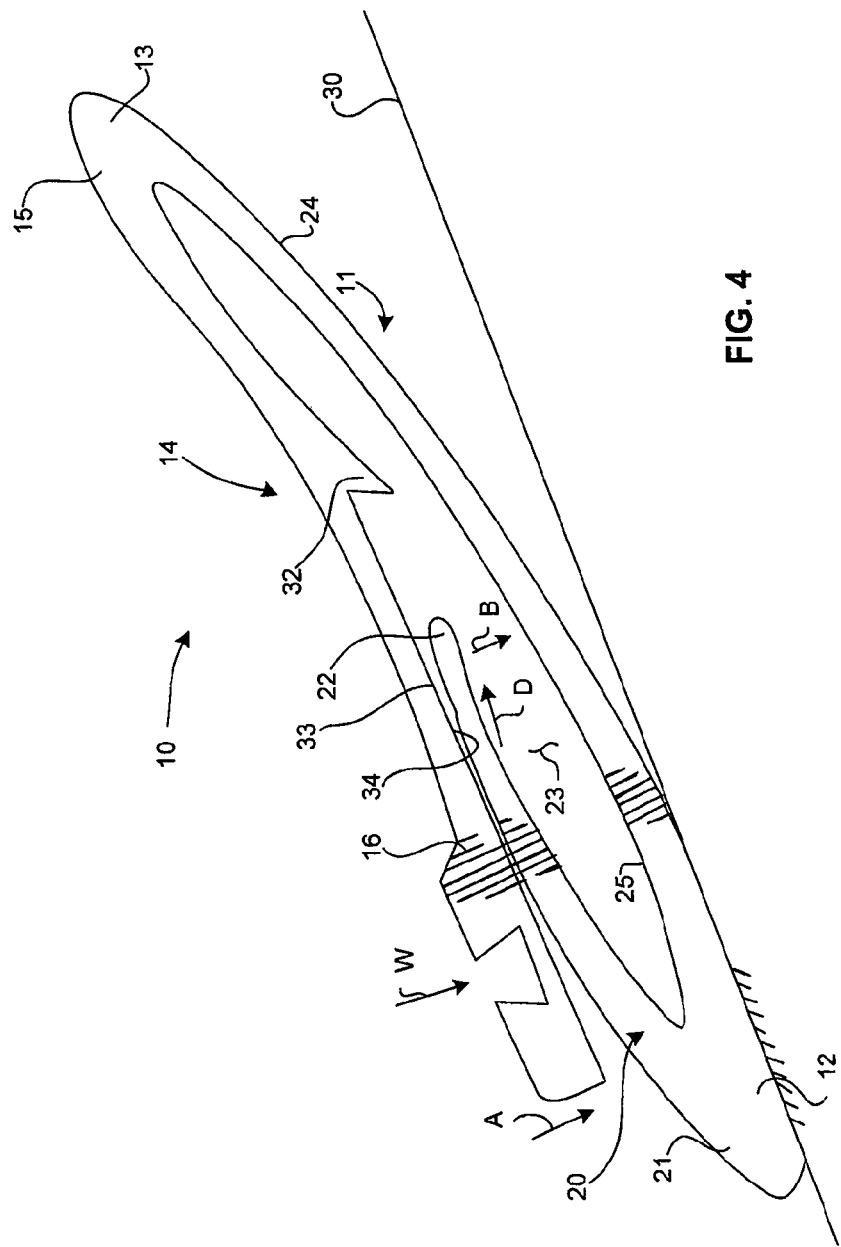
FIG. 4 is a side view illustrating the prosthetic foot of FIG. 2 at the impact of the heel.

FIG. 4 illustrates prosthetic foot 10 shortly after heel strike. After the bottom surface 24 on first bottom end 12 of resilient flexion bottom member 11 contacts ground 30, the user's weight, indicated by arrow W in FIGS. 3 to 6, compresses second toe end 16 downwardly in the direction of arrow A in FIGS. 3 and 4 such that lower contact surface 33 slidably contacts upper contact surface 34 and resilient flexion toe member 14 forces second heel end 22 of resilient flexion heel member 20 downwardly in the direction indicated by arrows B in FIGS. 3 and 4. Upper contact surface 34 slides over lower contact surface 33 in the direction indicated by arrow D in FIG. 4. As the user continues his stride after heel strike, prosthetic foot 10 rolls from the heel strike position of FIG. 4 to the mid-stance position illustrated in FIG. 5. In the mid-stance position, the individual's leg and upper body are generally directly above prosthetic foot 10 and a larger proportion of the individual's weight bears down on prosthetic foot 10.

Figure 5:
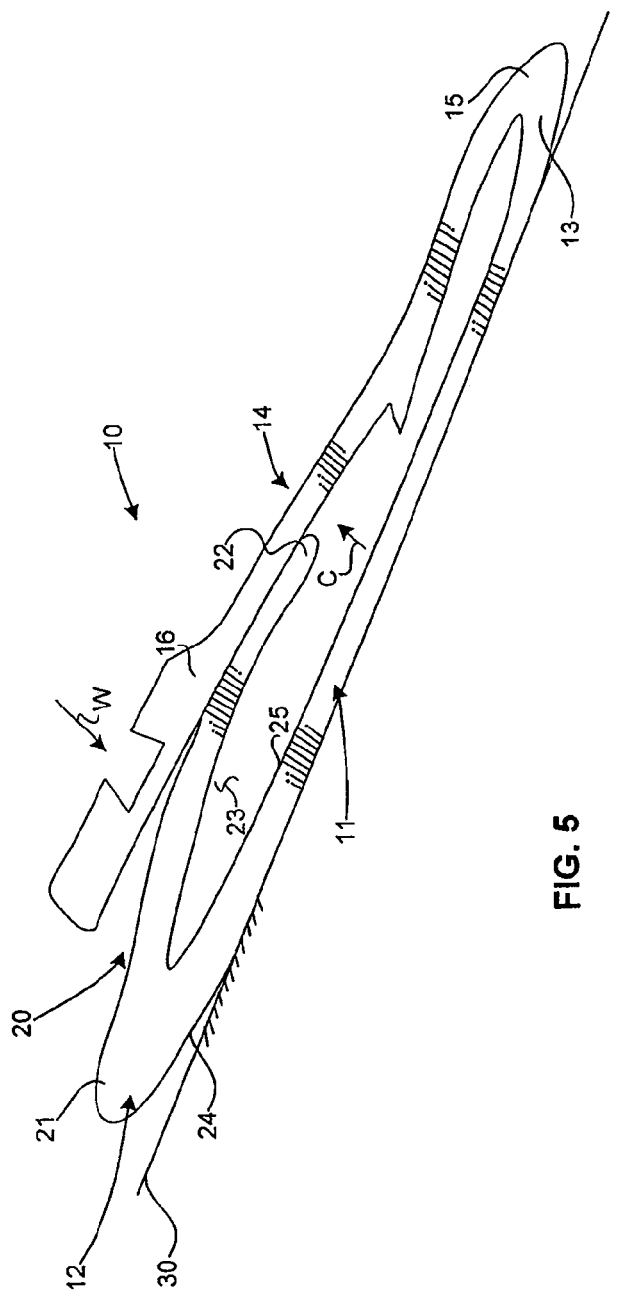
FIG. 5 is a side view illustrating the prosthetic foot of FIG. 2 after it has moved, or rolled, from the heel strike of FIG. 4 to mid-stance.

When prosthetic foot 10 rolls over bottom surface 24 from the heel strike position of FIG. 4 to the mid stance position of FIG. 5, the downward displacement and compression of resilient members 14 and 20 continues; however, at the same time resilient flexion bottom member 11 is compressed, resilient flexion bottom member 11 flexes upwardly in the direction of arrow C in FIGS. 3 and 5, and the convex curvature of resilient flexion bottom member 11 flattens. The flattening of resilient flexion bottom member 11 may initiate at, or shortly after heel strike, but the flattening is preferably clearly pronounced at mid-stance. As the individual continues his stride after prosthetic foot 10 reaches mid-stance, prosthetic foot 10 rolls from the mid-stance position of FIG. 5 to the toe strike position of FIG. 6.

Figure 6:
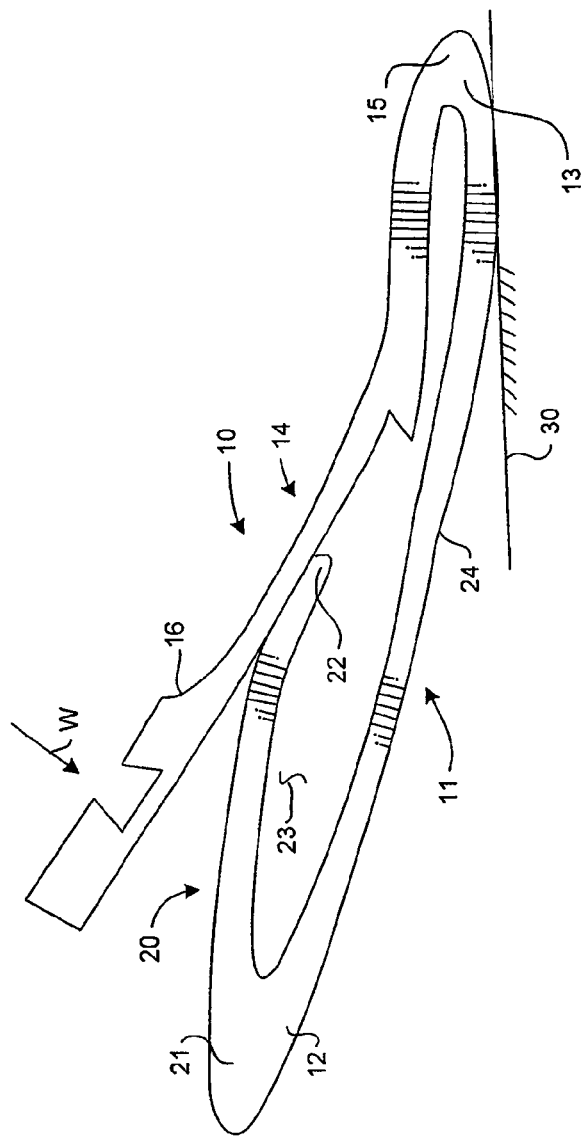
FIG. 6 is a side view illustrating the prosthetic foot of FIG. 2 after it has moved, or rolled, from the mid-stance of FIG. 5 onto the toe.

When the toe strike position is reached, as illustrated in FIG. 6, resilient flexion bottom member 11 normally has preferably resiliently returned at least in part to its original convex shape of FIG. 3, and resilient flexion members 14 and 20 have partially returned to their original unflexed position illustrated in FIG. 3. However, resilient flexion members 14 and 20 are normally still partially, downwardly compressed and flexed in the manner illustrated in FIG. 6. At toe strike, prosthetic foot 10 is generally behind the individual's upper body, as is normally the case when a person is walking. As the individual continues his stride, lifts prosthetic foot 10 off ground 30, and puts his other foot on the ground, prosthetic foot 10 regains its unflexed configuration illustrated in FIGS. 2 and 3.

As would be appreciated by those of skill in the art, it is possible to fabricate resilient flexion members 11, 14, 20 such that they are exceedingly stiff and will not resiliently flex at all when an individual wearing a prosthetic device on his leg walks on prosthetic foot 10. This would, of course, defeat the purpose of the device. The "stiffness" or resistance to flexure of resilient flexion members 11, 14, 20 can be adjusted as desired; however, the flexure of resilient flexion members 11, 14, 20 is adjusted such that prosthetic foot 10 will absorb at least a portion of the impact encountered by an individual when prosthetic foot 10 strikes and rolls over the ground. In an exemplary embodiment, various materials may be used to construct prosthetic foot 10, and the different materials result in different stiffness. Moreover, in an exemplary embodiment, resilient flexion members 11, 14, 20 are made of the same material or may be made of different materials. Some of the various materials include fiber glass, plastic, metal, carbon fiber, and the like.

In accordance with an exemplary embodiment, resilient flexion members 11, 14, 20 are made of glass fiber composite. The glass fiber composite may be a glass reinforced unidirectional fiber composite. In one embodiment, the fiber composite material is made of a weave of fibers and resin to produce a strong and flexible material. The fibers may be glass fibers or carbon fibers. Specifically, layers of fiber are impregnated with the resin, and a glass reinforcement layer is positioned between at least two fiber weave layers. Typically, several layers of the unidirectional fibers or tape are layered together to achieve the desired strength and flexibility. In one embodiment, the composite material is thermal formed and has a quick cure time, such as less than 60 minutes. In an exemplary embodiment, the composite material is designed to provide a desired mix of strength and flexibility. Adding more fiber to the material ratios increases the material strength but decreases the flexibility, and vice versa. In one embodiment, the composite material is about 50% resin and about 50% fiber.

In one embodiment, fastener holes are planned into the prosthetic foot pieces but not fully formed during the molding process. After removing the prosthetic foot pieces from the mold, the fastener holes may be enlarged to a final size (for example, by drilling or machining). In an exemplary embodiment, the placement of the fastener and fastener holes are designed to offer greater product flexibility. Specifically, the fastener holes are placed away from the end of the toe. This placement creates the option to machine the toe to create different prosthetic feet sizes based on a single mold design. In other words, the end of the toe can be machined off to create a smaller foot.

In addition to the composite layers, other options may be included in the prosthetic foot material. In an exemplary embodiment, a surfacing veil layer can be added to the top of toe member 14 (or any top surface of any component). The surfacing veil layer may also be described as a scrim layer. The surfacing veil layer chemically bonds to the exterior layer of the composite material. Moreover, the veil layer becomes an exposed, outer layer of the composite material. The veil layer may be a nonwoven carbon or fiber glass scrim that has absorbed resin from the composite material. Furthermore, the surfacing veil layer provides moisture protection. Another function of the surfacing veil layer may be to provide aesthetic options to the user. Specifically, the surfacing veil layer may include designs and patterns to enhance the aesthetic appeal of the prosthetic foot.

Figure 7:
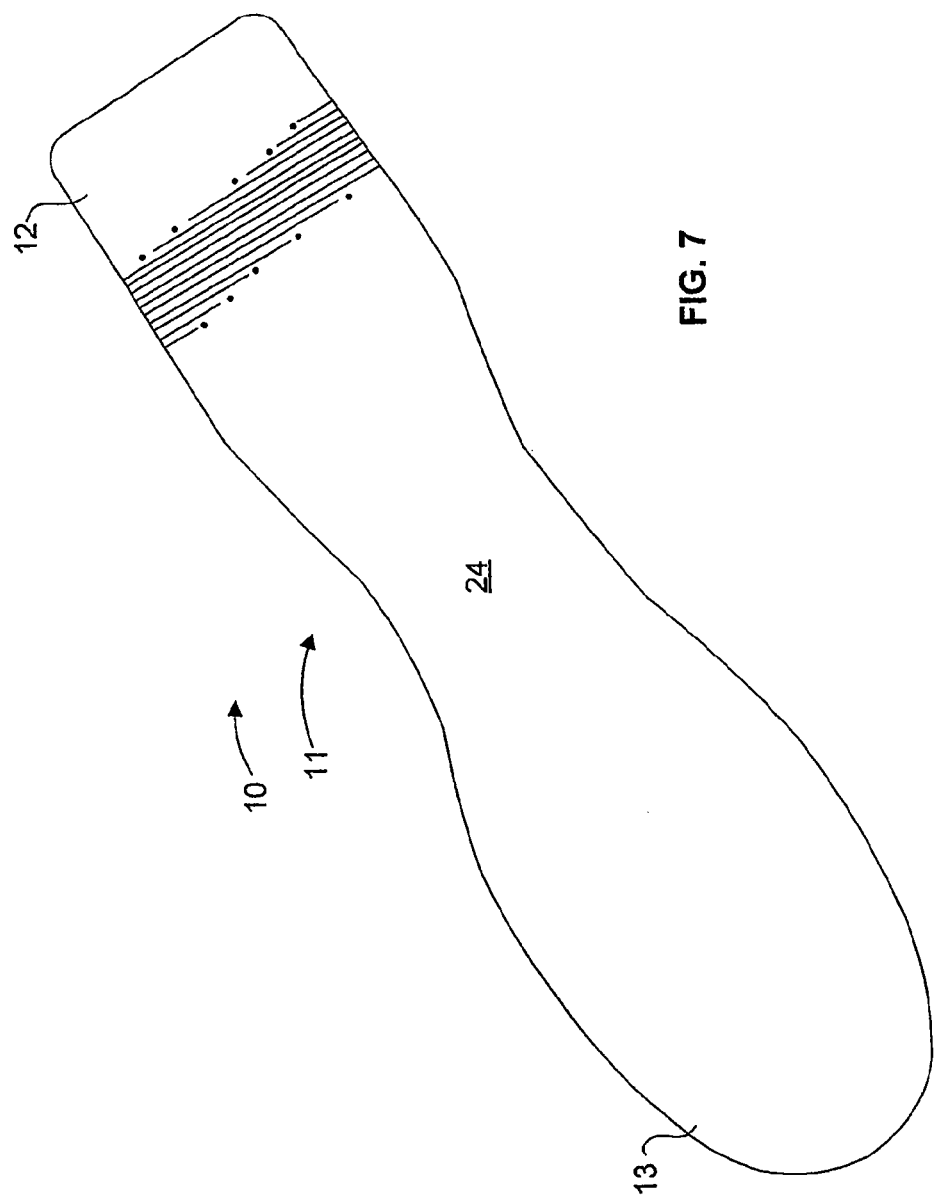
FIG. 7 is a bottom view illustrating the prosthetic foot of FIG. 2.

FIG. 7 illustrates a bottom view of an exemplary prosthetic foot, specifically the instep of the layout. In an exemplary embodiment, the middle section of bottom surface 24 is narrower than bottom ends 12, 13 of bottom member 11. The narrow middle section of bottom member 11 is configured to provide enhanced ground compliance for prosthetic foot 10. Ground compliance is the ability to react to stepping on uneven footing, such as unlevel ground or an object. The narrow middle section allows flexibility between first bottom end 12 and second bottom end 13 by way of lateral twisting.

In accordance with another exemplary embodiment and with reference to FIGS. 8 and 9, a prosthetic foot 10A is similar to prosthetic foot 10 and includes the same resilient bottom member 11. However, prosthetic foot 10A comprises a resilient heel member 20A that is shorter than heel member 20. Furthermore, a resilient toe member 14A includes a first toe end 15A similar to first toe end 15 of resilient flexion toe member 14. Resilient toe member 14A also comprises a second toe end 16A, which is similar to second toe end 16. However, second toe end 16A of resilient toe member 14A is shaped differently from second toe end 16 and includes an approximately orthogonal tongue 44 having an aperture 45 formed there through. Aperture 45 may be configured to receive a bolt 41 that secures a connector 40 to tongue 44. In an exemplary embodiment, connector 40 includes spaced apart legs 42, 43 that slide over the top of tongue 44. Each leg 42, 43 includes an aperture formed there through that is, if connector 40 is mounted on the top of tongue 44 in the manner illustrated in FIG. 8, in registration with aperture 45 such that bolt 41 can extend through all three apertures to secure connector 40 on tongue 44.

In one exemplary embodiment and with continued reference to FIGS. 8 and 9, a resilient elastomeric polymer bridge 46 is fixedly secured to the bottom of resilient flexion toe member 14A (or, if desired, to the top of second heel end 22A) and includes a smooth arcuate outer surface 46A that slides over the upper contact surface 34A of second heel end 22A when resilient flexion members 14A and 20A are compressed toward resilient flexion bottom member 11 by an individual's weight. Prosthetic foot 10A functions in substantially the same manner as prosthetic foot 10.

In another embodiment of the invention, resilient flexion heel member 20, 20A is removed and is not utilized in a foot 10, 10A. In a further exemplary embodiment, resilient flexion toe member 14, 14A is removed and is not utilized in a prosthetic foot 10, 10A, in which case second heel end 22A is shaped and dimensioned like second toe end 16, 16A to be attached to a prosthetic leg worn by an individual.

Instead of resilient flexion toe member 14, 14A extending upwardly over resilient flexion heel member 20, 20A in the manner illustrated in FIGS. 3-6 and 8, in still another exemplary embodiment, prosthetic foot 10, 10A is shaped and dimensioned such that resilient flexion heel member 20, 20A extends upwardly over resilient flexion toe member 14, 14A—in which case a portion of resilient flexion heel member 20, 20A is shaped to perform the function of second toe end 16 and to attach to a prosthetic leg worn by an individual.

Resilient flexion bottom member 11 and space 23 are important features of the prosthetic foot because they enable prosthetic foot 10 to roll over and traverse an upraised area 31 on the ground 30 without producing a "kick back" force that tends to force an amputee's leg rearwardly. Resilient flexion bottom member 11 deflects in the direction of arrow C (as shown in FIG. 3) to absorb forces produced by upraised area 31.

While it is presently preferred that resilient flexion bottom member 11 have a convex shape and bottom surface 24 in the manner illustrated in FIGS. 1-5 and 7, resilient flexion bottom member 11 can still deflect and function to absorb some forces (particularly those forces produced by an upraised member 31) if resilient flexion bottom member 11 is relatively flat in the manner indicated by dashed lines 11A in FIG. 8, or if resilient flexion bottom member 11 is concave in the manner indicated by dashed lines 11B in FIG. 8.

Figure 10:
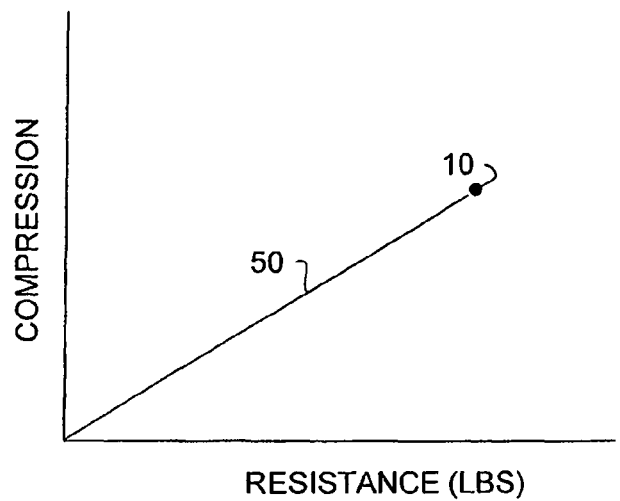
FIG. 10 is a graph generally illustrating the resistance-compression profile of a typical prior art prosthetic foot.
Figure 11:
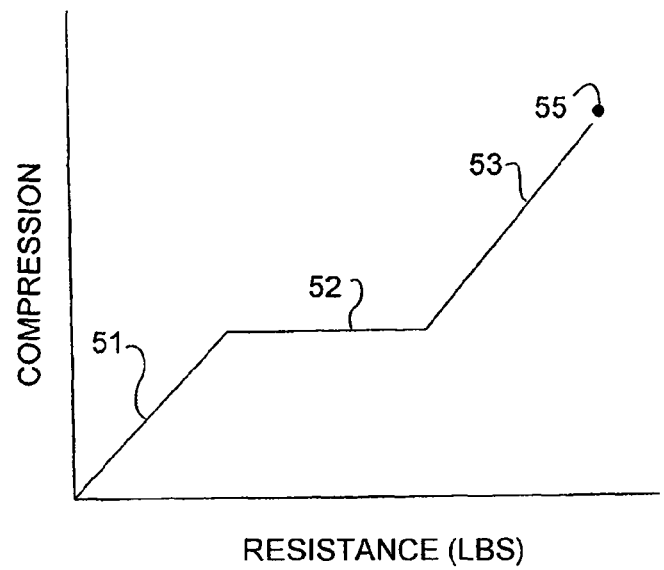
FIG. 11 is a graph generally illustrating the resistance-compression profile of an exemplary embodiment of a prosthetic foot.

FIG. 10 illustrates a resistance-compression graph generally representing a typical prior art prosthetic foot. As is indicated by line 50 in FIG. 10, when a prior art prosthetic foot is compressed, the resistance response comprises a steadily increasing resistive force up until the prosthetic foot breaks 54. In contrast, the exemplary prosthetic foot 10, 10A has a resistance-compression graph of the general type illustrated in FIG. 11, in which the resistive force increases as indicated by line 51, levels off as indicated by line 52, and then increases as indicated by line 53 up until the prosthetic foot breaks 55. In FIGS. 10 and 11, "compression" on the vertical axis of each graph indicates the distance that the foot is compressed toward the ground (or other surface) from its normal at rest configuration. The greater the compressive force that is applied to a prosthetic foot, the more the foot is flattened and pressed against the ground or another surface against which the foot is being pressed. In FIGS. 10 and 11, "resistance" in pounds on the horizontal axis of each graph indicates the compressive force required to compress the prosthetic foot through the distance indicated on the vertical axis.

In another exemplary embodiment, the prosthesis includes a resilient bladder 56 inserted intermediate resilient flexion members 20 and 11 (or resilient flexion members 14 and 11). The interior of bladder 56 is charged with air, water, or another desired fluid. In the event a liquid is utilized, bladder 56 can, if desired, be partially or completely filled. When an individual walks on the prosthetic foot, the resilient bladder 56 is compressed and distends laterally to absorb compressive pressure that is applied to bladder 56 when resilient flexion heel member 20 is displaced toward resilient flexion bottom member 11. When the compressive pressure wanes, and resilient flexion heel member 20 moves away from resilient flexion bottom member 11, bladder 56 resiliently returns to its original shape and dimension. The bladder 56 can, if desired, be inflated with a desired fluid to a selected pressure greater than ambient pressure, in the same way that a tire on a vehicle is filled with air to a selected pressure greater than ambient pressure.

Figure 12:
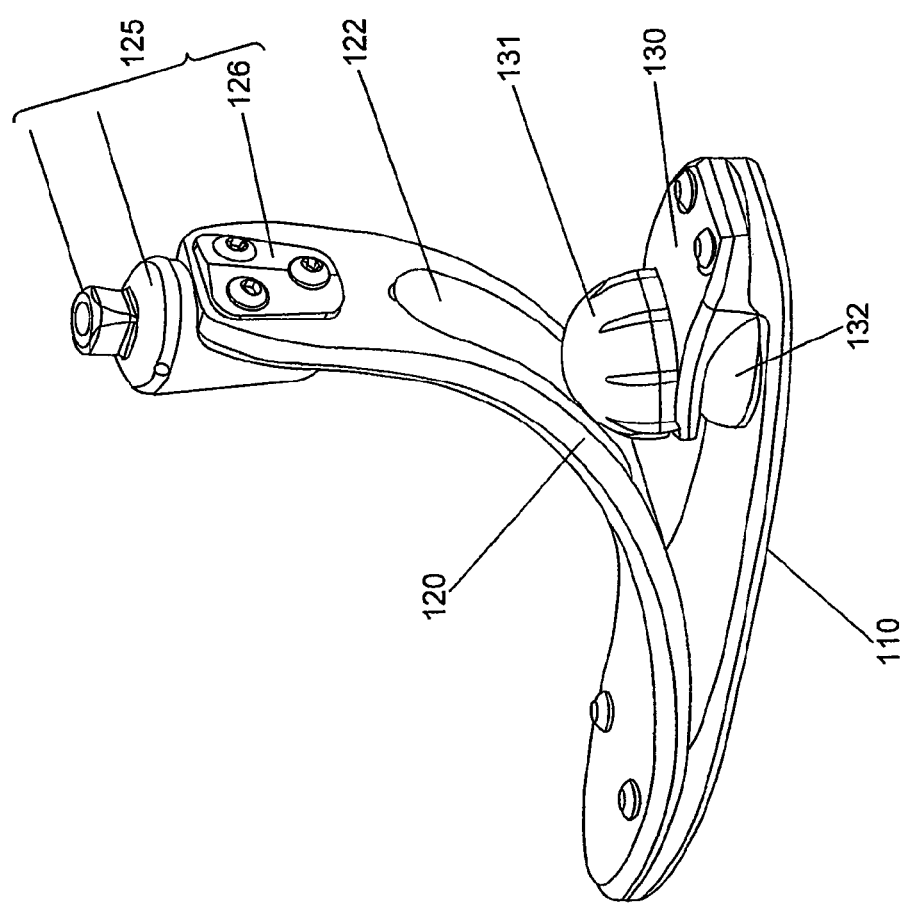
FIG. 12 is a perspective view of an exemplary embodiment of a prosthetic foot.

In accordance with an exemplary embodiment and with reference to FIG. 12, a prosthetic foot 100 comprises a bottom member 110, a toe member 120, and a heel member 130. The prosthetic foot 100 is configured to promote increased muscle activity and promote increased stability in the user. The increased muscle activity is the result of prosthetic foot 100 recruiting the use of secondary and tertiary muscle groups not typically employed in a walking motion. The stance phase is approximately 60% of the walking cycle, and may be more difficult in terms of stability. The recruitment of the secondary and tertiary muscle groups increases their muscle strength, which in turn increases the static and dynamic stability of the user. Furthermore, prosthetic foot 100 and strengthened muscle groups reduce the forward lean of the user.

As previously mentioned, the primary anterior muscle responsible for dorsiflexion (sagittal plane motion) is the anterior tibialis. Dorsiflexion is the voluntary ankle motion that elevates the foot upwards, or towards the midline of the body. The primary posterior muscle responsible for plantarflexion is the gastro-soleus complex. It is a combination of two muscles working in conjunction: the gastrocnemius and the soleus. Plantarflexion is the voluntary ankle motion that depresses the foot downwards, or away from the midline of the body.

With respect to the walking motion, prosthetic foot 100 is configured to increase the surface-to-foot contact through the gait cycle. The increased surface contact allows a smoother gait cycle, and increases stability in comparison to the typical prior art. In exemplary embodiments, the underside of bottom member 110 has different contours that provide increased surface contact for different types of uses. In a first example and with reference to FIG. 13A, a general convex shape of bottom member 110 facilitates a rocking motion from heel-to-toe during the gait cycle. The convex shape is designed to increase stability by supplying surface contact of at least about 33% of the bottom surface during the heel strike and toe off motions, and about 60% surface contact during the mid-stance phase. Furthermore, a load center 101 of the supported leg is at approximately ⅔ of the bottom surface from the toe, ⅓ of the bottom surface from the heel. In other words, load center 101 is not at a radial center of the walking path. This off-set load center and surface area contact is designed to provide symmetry and balance for the prosthetic foot user.

Figure 13B:
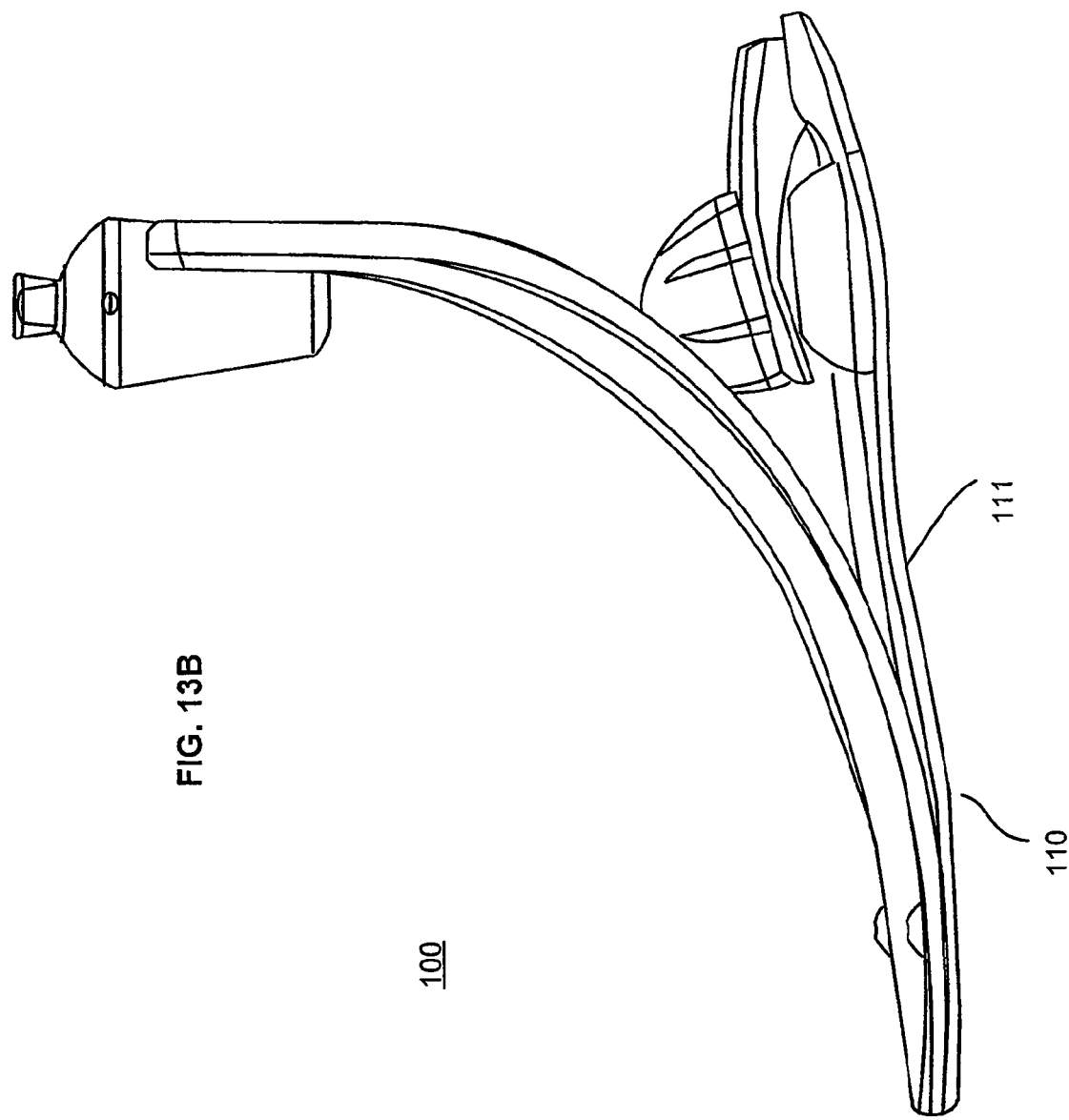
FIG. 13B is a side view of an exemplary prosthetic foot with an undulating bottom surface.

In a second example of different contours and with reference to FIG. 13B, bottom member 110 may have a "wave" shape, or an undulating contour. The wave-contour of bottom member 110 is designed for active users, so that the elevated middle portion will absorb a strong impact like running. The bottom member 110 has the toe and heel sections curved slightly upwards, along with an elevated section 111 in the middle of the foot. In one embodiment, elevated section 111 is a gap of about ⅜ inch from the surface. Moreover, in an exemplary embodiment, the "wave" shape of bottom member 110 may be mathematically described by a spline equation, specifically a non-uniform rational basis spline (NURBS curve).

Figure 14:
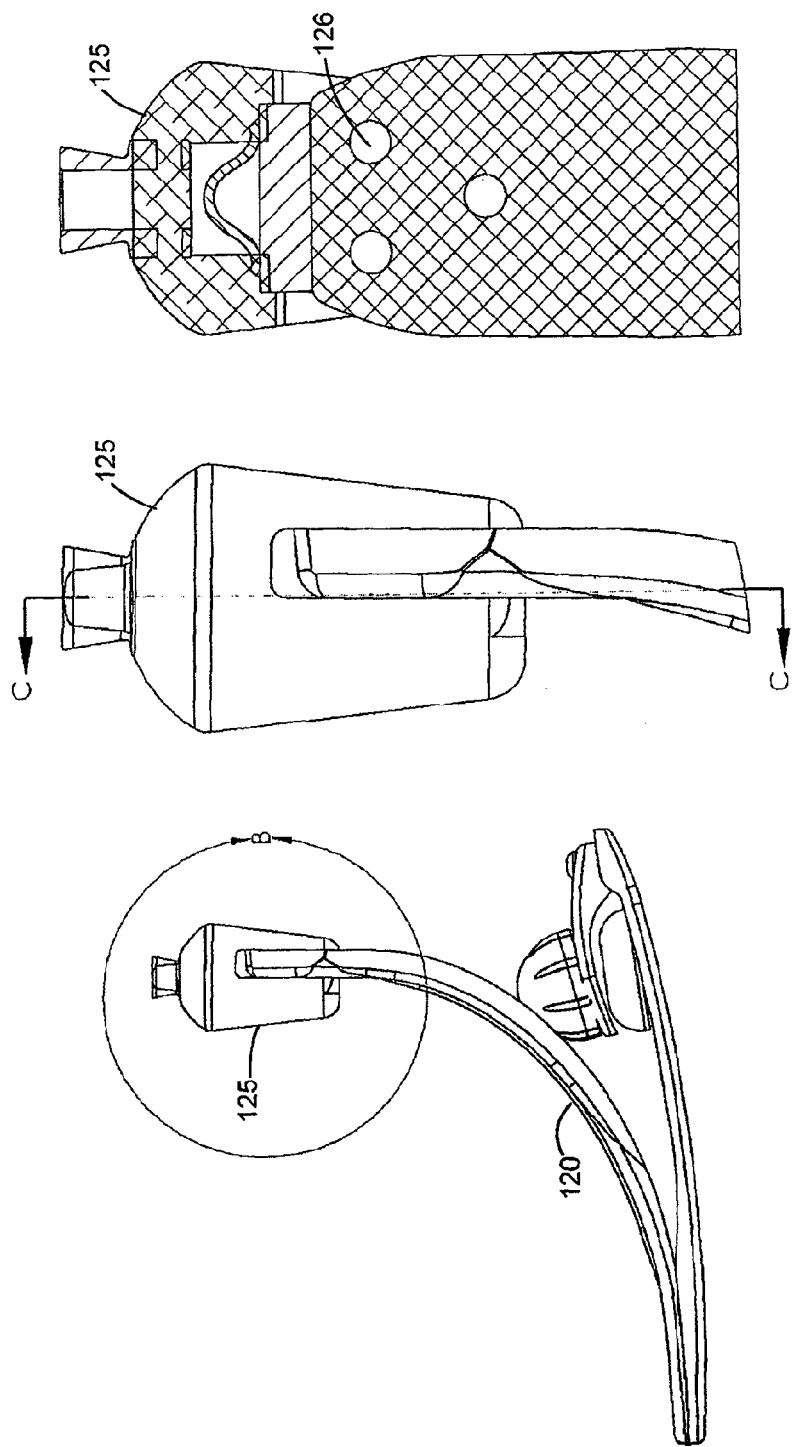
FIG. 14 is a perspective view of a prosthetic foot with an exemplary connector spring clamp.

Prosthetic foot 100, in one embodiment, further comprises a connector spring clamp 125 that is coupled to toe member 120 and is configured to attach to a prosthetic leg. In one embodiment and with reference to FIG. 14, connector spring clamp 125 is fastened to toe member 120 using screws 126. Furthermore, connector spring clamp 125 comprises a vertical spring, which may be a coil spring or other compression spring. The top of connector spring clamp may be a standard connector confirming to industry regulations for prosthetic leg attachment.

In addition, heel member 130 may comprise at least one bumper, such as primary bumper 131 or secondary bumper 132. The primary bumper 131 is attached to heel member 130 and also in contact with the underside of toe member 120. The primary bumper is designed to provide a damping resistance while cushioning the deflection of toe member 120 during use. In an exemplary embodiment, the underside of toe member 120 includes a grooved area 122 that is in contact with primary bumper 131. The grooved area provides additional surface area contact with primary bumper 131 and therefore more stability. With respect to the other possible bumper, secondary bumper 132 is in coupled between heel member 130 and bottom member 110. The secondary bumper 132 is also configured to provide a damping resistance while cushioning the deflection of heel member 130 during use.

In accordance with another exemplary embodiment, a prosthetic foot device may comprise a toe member and a bottom member without a heel member. Specifically, a bumper may be connected to either the bottom member or the toe member, and be configured to contact the opposite member. The bumper connection between the toe member and the bottom member facilitates energy transfer during the gait cycle. In one embodiment, the bumper is located towards the rear of the toe and bottom members.

Figure 15A:
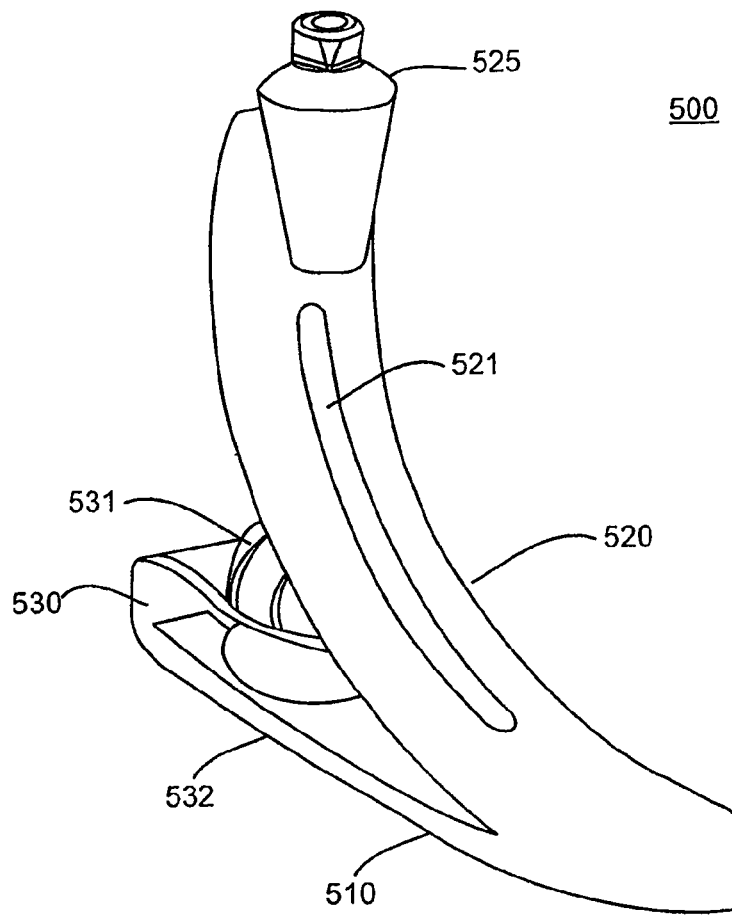
FIGS. 15A-15C illustrate various perspective views of an exemplary prosthetic foot having a midline toe slot.
Figure 15B:
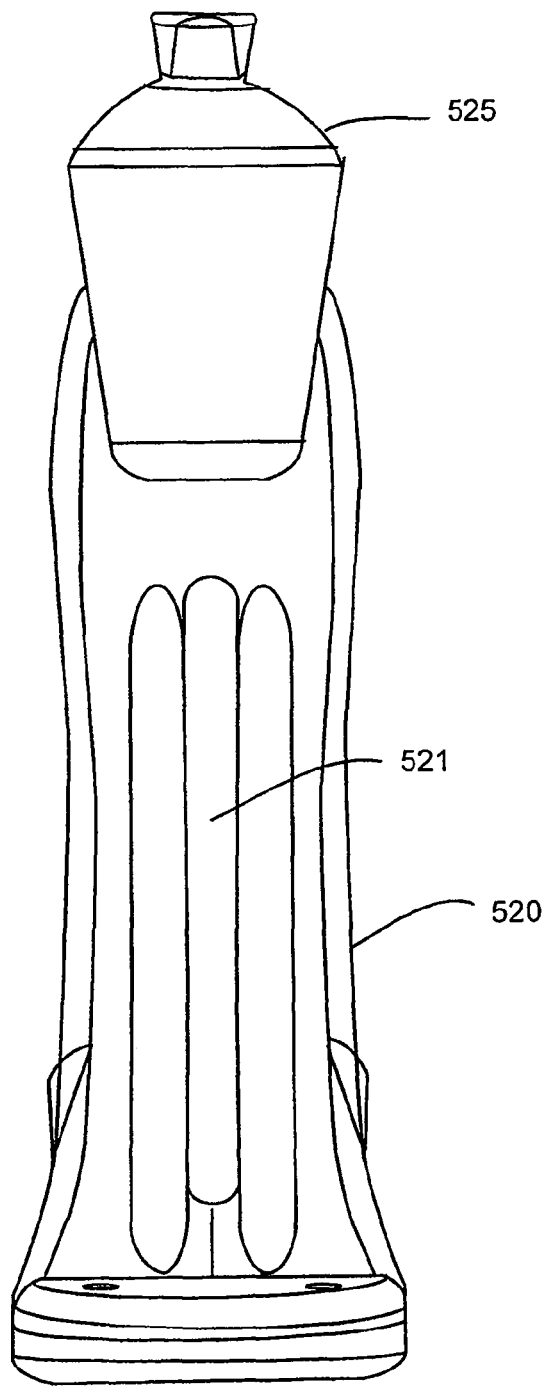
Figure 15C:
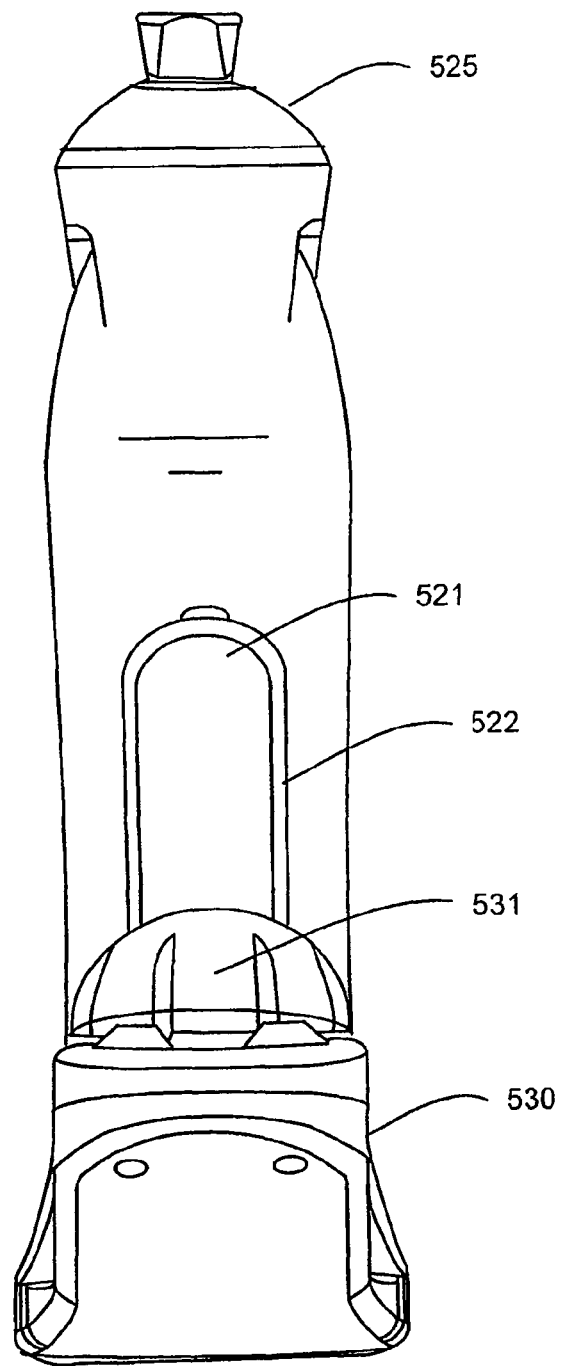

Additional prosthetic feet embodiments similar to prosthetic foot 100 have also been contemplated. One such embodiment is a prosthetic foot with increased flexibility. One design capable of achieving additional flexibility includes a lengthwise slot dividing a toe member. The slot increases toe member flexibility in two ways. First, the slot reduces the amount of material of the toe member, thereby reducing the resistance to plantarflexion and dorsiflexion movement. Second, locating the lengthwise slot at about the midline of the prosthetic foot enables lateral twisting, thereby mimicking a pronated position and a supinated position. In accordance with an exemplary embodiment, and with reference to FIGS. 15A-15C, a prosthetic foot 500 comprises a bottom member 510, a toe member 520 with a toe slot 521, a heel member 530, and a connector 525. Prosthetic foot 500 may further comprise a primary bumper 531 and/or a secondary bumper 532. Also, as shown in FIG. 15C, toe member 520 may include a grooved area 522 on the backside that is configured to be in contact with primary bumper 531. The grooved area 522 provides additional surface area contact with primary bumper 531 and therefore more stability.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. Furthermore, couple may mean that two objects are in communication with each other, and/or communicate with each other, such as two pieces of hardware. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect.

It should be appreciated that the particular implementations shown and described herein are illustrative of various embodiments including its best mode, and are not intended to limit the scope of the present disclosure in any way. For the sake of brevity, conventional techniques for signal processing, data transmission, signaling, and network control, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical communication system.

While the principles of the disclosure have been shown in embodiments, many modifications of structure, arrangements, proportions, the elements, materials and components, used in practice, which are particularly adapted for a specific environment and operating requirements without departing from the principles and scope of this disclosure. These and other changes or modifications are intended to be included within the scope of the present disclosure and may be expressed in the following claims.

What is claimed is:

1. A prosthetic foot device comprising:
   a bottom member comprising a front end and a back end and an intermediate section spanning between and connecting said front end and said back end, wherein the bottom member is convex from said front end to said back end with respect to the ground, and wherein said back end is configured to contact the ground during a gait cycle;
   a toe member comprising a front end and a back end, wherein said front end is connected to said front end of said bottom member, wherein said toe member extends upwardly from said front end, and, having said back end spaced apart from said front end, and wherein said back end of the bottom member is not connected to said front end of the toe member;
   a connector attached to said back end of said toe member configured for coupling the prosthetic foot device to a prosthetic leg device; and
   a bumper coupled to an upper surface of the back end of said bottom member and in contact with the underside of said toe member.

2. The prosthetic foot of claim 1, wherein 90% or more of energy stored during a heel strike phase is transferred to said toe member for assisting a toe-off phase.

3. The prosthetic foot of claim 1, wherein at least one of said bottom member and said toe member is made of a glass and fiber composite, wherein said glass and fiber composite comprises a fiber weave layer of about 50% fiber and about 50% resin, and a glass reinforcement layer positioned between at least two fiber weave layers.

4. The prosthetic foot of claim 3, further comprising a surfacing veil layer on a surface of said toe member, wherein said surfacing veil layer chemically bonds to said glass and fiber composite.

5. The prosthetic foot device of claim 1, wherein said intermediate section of said bottom member has a convex shape with respect to the ground.

6. The prosthetic foot device of claim 5, wherein at least 33% of said bottom member is in contact with a surface during heel strike and toe-off motions of a gait cycle.

7. The prosthetic foot device of claim 5, wherein at least 60% of said bottom member is in contact with a surface during a mid-stance phase of a gait cycle.

8. The prosthetic foot device of claim 5, further comprising a heel member connected to said back end of said bottom member, wherein said heel member extends upwardly from said back end.

9. The prosthetic foot device of claim 8, further comprising a secondary bumper coupled to the heel member and in contact with said back end of said bottom member.

10. The prosthetic foot device of claim 9, wherein said secondary bumper is configured to provide a damping resistance while cushioning the deflection of said heel member during use.

11. The prosthetic foot device of claim 8, wherein said bottom member, said heel member, and said toe member are chemically bonded.

12. The prosthetic foot device of claim 1, wherein the prosthetic leg device has a load center set back approximately ⅔ of said bottom surface from the front end.

13. The prosthetic foot device of claim 1, wherein said bumper is configured to provide a damping resistance while cushioning the deflection of said toe member during use.

14. The prosthetic foot of claim 1, wherein a loading response during a heel strike phase compresses said toe member and causes a deflection of a rear portion of said bottom member.

15. The prosthetic foot of claim 14, wherein an upward deflection of at least one of said bottom member and said toe member stores energy during a transition from the heel strike phase to a toe-off phase of the gait cycle, and wherein 90% of more of the energy stored during the heel strike phase is transferred to said toe member for assisting the toe-off phase.

16. The prosthetic foot of claim 1, further comprising an elastomeric layer positioned between a front portion of the toe member and a front portion of the bottom member, wherein the elastomeric layer facilitates the connection between the toe member and the bottom member using adhesive layers on either side of said elastomeric layer.

* * * * *